United States Patent [19]

Silverman et al.

[11] Patent Number: 4,466,960

[45] Date of Patent: Aug. 21, 1984

[54] ANALGESIC-DIURETIC COMPOSITIONS

[75] Inventors: Harold I. Silverman, Framingham, Mass.; Edward L. Steinberg, Long Beach, N.Y.

[73] Assignee: Thompson Medical Co., Inc., New York, N.Y.

[21] Appl. No.: 543,239

[22] Filed: Oct. 18, 1983

[51] Int. Cl.$^3$ .................. A61U 31/52; A61U 31/165; A61U 33/02

[52] U.S. Cl. .................................. 424/166; 424/253; 424/324

[58] Field of Search ........................ 424/253, 324, 166

[56] References Cited

PUBLICATIONS

Chem. Abst., vol. 97 (1982), 168928k.

Primary Examiner—Stanley J. Friedman
Attorney, Agent, or Firm—Kenyon & Kenyon

[57] ABSTRACT

Pharmaceutical compositions designed for the relief of premenstrual syndrome are disclosed which comprise acetaminophen, caffeine, a diuretic ammonium salt and an antihistamine.

10 Claims, No Drawings

ANALGESIC-DIURETIC COMPOSITIONS

The term "premenstrual syndrome" is generally used to describe a group of physical and mental symptoms which occur cyclically beginning seven to 14 days prior to menses, with an absence of symptoms for at least seven days after menses ends. Mental symptoms may range from slight irritability and lethargy to incapacitating depression. Physical symptoms include headaches, joint pains, cramps, bloating, congestion and tenderness in the mammary and vaginal areas.

A number of compositions are available which are designed to provide relief for one or more of the symptoms of premenstrual syndrome. Typically, these products are designed to reduce pain or reduce water retention. Formulations such as Midol ® (Glenbrook Laboratories) and Pamprin ® (Chattem Laboratories) have the analgesics aspirin and acetaminophen as their major active components, respectively, whereas products such as Aqua-Ban (Thompson Medical Co.) are formulated primarily as diuretics. A composition designed to maximize the delivery of compounds useful for the relief of the symptoms of premenstrual syndrome has not heretofore been available.

Therefore, it is an object of the present invention to provide a pharmaceutical composition designed for the relief of a broad spectrum of premenstrual syndrome-associated symptoms.

It is a further object of the present invention to provide a pharmaceutical unit dose form which is effective to deliver effective amounts of analgesic, diuretic, anti-depressive, and anti-cramping compounds to a patient via oral administration.

Other objects, advantages and novel features of the present invention will be apparent to those skilled in the art from the following description and appended claims.

BRIEF DESCRIPTION OF THE INVENTION

The objects of the present invention are achieved by a solid oral pharmaceutical composition which comprises a combination of acetaminophen, a diuretic ammonium salt, caffeine and an antihistamine, in amounts effective for the substantial relief of the pain, bloating, cramping and lethargy commonly associated with premenstrual syndrome. Effective compositions formulated in accord with the present invention will comprise about 40–60% acetaminophen, about 25–45% of a diuretic ammonium salt, about 5–20% caffeine and about 0.5–5% of pyrilamine maleate, all percentages being calculated as percentages of the total active ingredients on a per weight basis.

DETAILED DESCRIPTION OF THE INVENTION

The pharmaceutical compositions of the present invention will comprise about 40–60%, preferably about 50–55% by weight of the non-salicylate analgesic acetaminophen. Acetaminophen is especially useful for those patients who cannot tolerate the salicylate analgesics such as aspirin. It acts to generally relieve the pain associated with headache, dysmenorrhea, myalgias, neuralgias, joint pains and the like. A typical unit dose form such as a tablet or encapsulated powder formulated in accord with the present invention will comprise about 300–700 mg of acetaminophen, preferably about 450–550 mg.

The composition of the present invention will also comprise about 25–45%, preferably about 30–40%, of a diuretic ammonium salt such as ammonium acetate, ammonium citrate, ammonium nitrate, ammonium chloride or mixtures thereof. These ammonium salts are osmotic diuretics and function to relieve the discomfort caused by water retention, bloating and pelvic congestion associated with premenstrual syndrome and dysmenorrhea. Ammonium chloride is the preferred diuretic for employment in the present compositions, and a unit dose form will comprise about 250–1000 mg of this compound, preferably about 300–500 mg.

The compositions of the present invention will also comprise about 5–20% caffeine, most preferably about 8–15%. Caffeine or its acid salts function as central nervous system stimulants which act to relieve the fatigue and lethargy which are often associated with premenstrual syndrome, and counteract the potential sedative activity of the antihistamine component. Caffeine is also a mild loup diuretic which functions by decreasing the proximal tubular reabsorption of water and sodium ions in the kidney. A synergistic effect may be expected when caffeine is combined with the ammonium salt diuretics. The diuretic activity is useful to relieve the physical tension and fluid retention associated with premenstrual syndrome or menstruation. A unit dose form of a composition of the present invention will preferably comprise about 50–250 mg of caffeine, most preferably 75–200 mg.

The compositions of the present invention will also comprise about 0.5–5%, preferably about 1–3%, of an antihistamine such as diphenhydramine, promethazine, pyrilamine maleate and the like. These compounds function to reduce the cramping and backache commonly associated with premenstual syndrome. Pyrilamine maleate is the preferred antihistamine for use in the present compositions, and a unit dose form will preferably comprise about 10–50 mg of this compound.

Therefore, a preferred anti-premenstrual syndrome composition prepared in accord with the present invention will comprise about 50–55% acetaminophen, about 30–40% ammonium chloride, about 8–15% caffeine and about 1–3% pyrilamine maleate, all percentages being per weight percentages based on the total weight of the active ingredients.

The compositions of the present invention are typically formulated for oral administration, and thus may be encapsulated in hard or soft gelatin capsules in the form of substantially-dry powders or may be mixed with suitable adjuvants such as binders, dispersing agents, lubricants and disintegrators and compressed into tablets by methods well known in the encapsulating or tabletting art.

The following example is intended to be representative of a typical procedure which may be employed to prepare tablets comprising the present compositions.

Acetaminophen (5000 g), pyrilamine maleate (150 g), caffeine (1000 g) and ammonium chloride (3250 g) are mixed thoroughly in a ribbon blender with 225 g polyvinypyrrolidone (dispersing agent/binder) and 617 g lactose (binder). The mixture is passed through a 40 mesh screen and 100 l of ethanol added (3A-200 proof). The wet mass is kneaded well and then is passed through a 4 mesh screen and the resultant granules are dried for 18 hours at 50° C. The dried granules are passed through a 20 mesh screen. A mixture of 90 g of stearic acid (lubricant), 135 g of talc (lubricant) and 432.5 g of corn starch (disintegrator) is passed through a 60 mesh screen and tumbled with the granules. The resultant dry mixture is compressed into about $1 \times 10^5$ individual tablets of about 1090 mg each via a 7/16 inch standard deep punch. Following tablet compression, the tablets are enteric coated using suitable polymeric materials such as cellulose acetate phthalate, hydroxy ethyl cellulose phthalate and other related phthalic acid cellulose derivatives which are known to be useful in the art of delaying tablet disintegration in the gastrointestinal tract. Each tablet contained a dose of about 325 mg of ammonium chloride, about 100 mg of caffeine, about 15 mg of pyrilamine maleate and about 500 mg of acetaminophen. Oral ingestion of 1-2 of the tablets every four hours is expected to provide effective multisymptom relief of premenstrual syndrome.

The identity and amount of the inert adjuvants may be varied in accord with accepted pharmaceutical compounding practices. For example, other or additional lubricants such as calcium or magnesium stearate or hydrogenated vegetable oils would be expected to be useful to prepare tablets incorporating the present compositions, as would binders such as gelatin, sucrose, glucose, vegetable gums and the like, dispersing agents such as microcrystalline cellulose, dextrose and amylose and disintegrating aids such as kaolin, algins and other vegetable starches. The tablets may also be coated, flavored and/or colored by methods well known in the art, employing various waxes, glazes, dyes and the like.

Alternatively, an effective amount of the dry active ingredient-containing granules may be encapsulated, i.e., in hard or soft gelatin capsules, and ingested orally in that unit dosage form to achieve the desired symptomatic relief.

While certain representative embodiments of the invention have been described herein for purposes of illustration, it will be apparent to those skilled in the art that modifications may be made therein without departing from the spirit and scope of the invention.

We claim:

1. A solid oral pharmaceutical composition comprising a mixture of active ingredients which comprises about 40-60% acetaminophen, about 5-20% caffeine, about 25-45% of a diuretic ammonium salt selected from the group consisting of ammonium acetate, ammonium citrate, ammonium nitrate, ammonium chloride and mixtures thereof; and about 0.5-5% of an antihistamine selected from the group consisting of diphenhydramine, promethazine and pyrilamine maleate.

2. The pharmaceutical composition of claim 1 wherein the mixture comprises about 50-55% acetaminophen, about 8-15% caffeine, about 30-40% ammonium salt and about 1-3% antihistamine.

3. The pharmaceutical composition of claim 2 wherein the ammonium salt is ammonium chloride.

4. The pharmaceutical composition of claim 3 wherein the antihistamine is pyrilamine maleate.

5. A pharmaceutical unit dose form comprising a tablet comprising the composition of claim 1.

6. The unit dose form of claim 5 wherein the tablet comprises about 450-550 mg acetaminophen, about 300-500 mg ammonium salt, about 75-200 mg caffeine and about 10-50 mg of antihistamine.

7. The dose form of claim 6 wherein the tablet further comprises an enteric coating.

8. The unit dose form of claim 7 wherein the tablet comprises about 325 mg ammonium chloride, about 500 mg acetaminophen, about 100 mg caffeine, and about 15 mg of pyrilamine maleate.

9. A method of relieving the symptoms of premenstrual syndrome which comprises orally administering an effective amount of the composition of claim 1.

10. A method of relieving the symptoms of premenstrual syndrome which comprises orally administering the dose form of claim 8.

* * * * *